United States Patent
Uozumi et al.

(10) Patent No.: US 7,897,817 B2
(45) Date of Patent: Mar. 1, 2011

(54) RESIN-PLATINUM COMPLEX AND RESIN-SUPPORTED PLATINUM CLUSTER CATALYST

(75) Inventors: Yasuhiro Uozumi, Okazaki (JP); Yoichi Yamada, Okazaki (JP); Takayasu Arakawa, Okazaki (JP)

(73) Assignee: Inter-University Research Institute Corporation National Institutes of Natural Sciences, Tokyo (JP)

( * ) Notice: Subject to any disclaimer, the term of this patent is extended or adjusted under 35 U.S.C. 154(b) by 0 days.

(21) Appl. No.: 11/885,734

(22) PCT Filed: Dec. 1, 2005

(86) PCT No.: PCT/JP2005/022068

§ 371 (c)(1),
(2), (4) Date: Sep. 5, 2007

(87) PCT Pub. No.: WO2006/095477

PCT Pub. Date: Sep. 14, 2006

(65) Prior Publication Data

US 2008/0176739 A1    Jul. 24, 2008

(30) Foreign Application Priority Data

Mar. 9, 2005    (JP) .............................. 2005-064913

(51) Int. Cl.
*C07C 49/00*    (2006.01)
(52) U.S. Cl. ........................ 568/303; 502/152; 556/137
(58) Field of Classification Search ................. 502/152; 556/137, 136; 568/303
See application file for complete search history.

(56) References Cited

U.S. PATENT DOCUMENTS 4,797,393 A * 1/1989 Farrell et al. ................. 514/188

(Continued)

FOREIGN PATENT DOCUMENTS

JP    11-309368    11/1999

(Continued)

OTHER PUBLICATIONS

Deese, W; Johnson, D; Synthesis of Pyrazolide-Bridged Heterometallic Binuclear Complexes. J. Organometallic Chem., 232(1982) 325-333.*

(Continued)

*Primary Examiner*—Stuart Hendrickson
*Assistant Examiner*—Richard M Rump
(74) *Attorney, Agent, or Firm*—Jenkins, Wilson, Taylor & Hunt, P.A.

(57) ABSTRACT

To provide a catalyst that has sufficient catalytic activity as a platinum catalyst and yet is readily separated from a target material and can be reused. A resin-supported platinum cluster catalyst containing a resin layer comprising a platinum particle core, the average diameter of which is from 1 nm to 10 nm, and a compound containing nitrogen (general formula $R^1NH_2$) surrounding the core. This catalyst can be obtained by forming a platinum complex from a compound containing nitrogen represented by the general formula $R^1NR^2{}_2$ (in the formula, $R^1$ represents a carrier with a hydrophilic molecular chain and $R^2$ represents a hydrogen atom, an alkyl group and the like) and a platinum compound represented by the general formula $M(PtX_{4-n}R^3{}_n)_m$ (in the formula, M represents an alkali metal and the like, X represents a halogen atom and the like, $R^3$ represents an unsaturated organic ligand, n represents an integer from zero to four and m represents an integer indicating the electrical charge of the metal, M) and allowing this platinum complex to react with a reducing agent in an aqueous solvent.

13 Claims, 1 Drawing Sheet

U.S. PATENT DOCUMENTS

2004/0102631 A1    5/2004    Uozumi

FOREIGN PATENT DOCUMENTS

| JP | 2003-236388 | 8/2003 |
| WO | WO00/13794 | 3/2000 |
| WO | WO02/072644 | 9/2002 |
| WO | WO03/009887 A2 * | 2/2003 |
| WO | WO2006/095477 | 9/2006 |

OTHER PUBLICATIONS

Uozumi, Y.; Nakao, R.; Angew Chem. Int. Ed. 2003, 42(2). 194-197.*
Mallat et al., Oxidation of Alcohols with Molecular Oxygen on Solid Catalysts, Chem. Rev. 2004, 104, 3037-3058.
International Preliminary Report on Patentability corresponding to International Patent Application No. PCT/JP2005/022068 dated Aug. 29, 2006.
International Search Report corresponding to International Patent Application No. PCT/JP2005/022068 dated Feb. 28, 2006.
Kirin et al., "Synthesis and Characterization of CuII Complexes with Amino Acid Substituted Di(2-pyridyl)amine Ligands," European Journal of Inorganic Chemistry. vol. 2007, No. 23 pp. 3686-3694 (2007).
Uozumi et al., "Development of an amphiphilic resin-dispersion of nanopalladium catalyst: Design, preparation, and its use in aquacatalytic hydrodechiorination and aerobic oxidation," Journal of Organometallic Chemistry. vol. 692 pp. 420-427 (2007).
Yamada, Y., Test Report. Natural Science Research Agency: Molecular Science Laboratory. pp. 5-7. Jul. 12, 2006. (Translation).

* cited by examiner

FIGURE 1
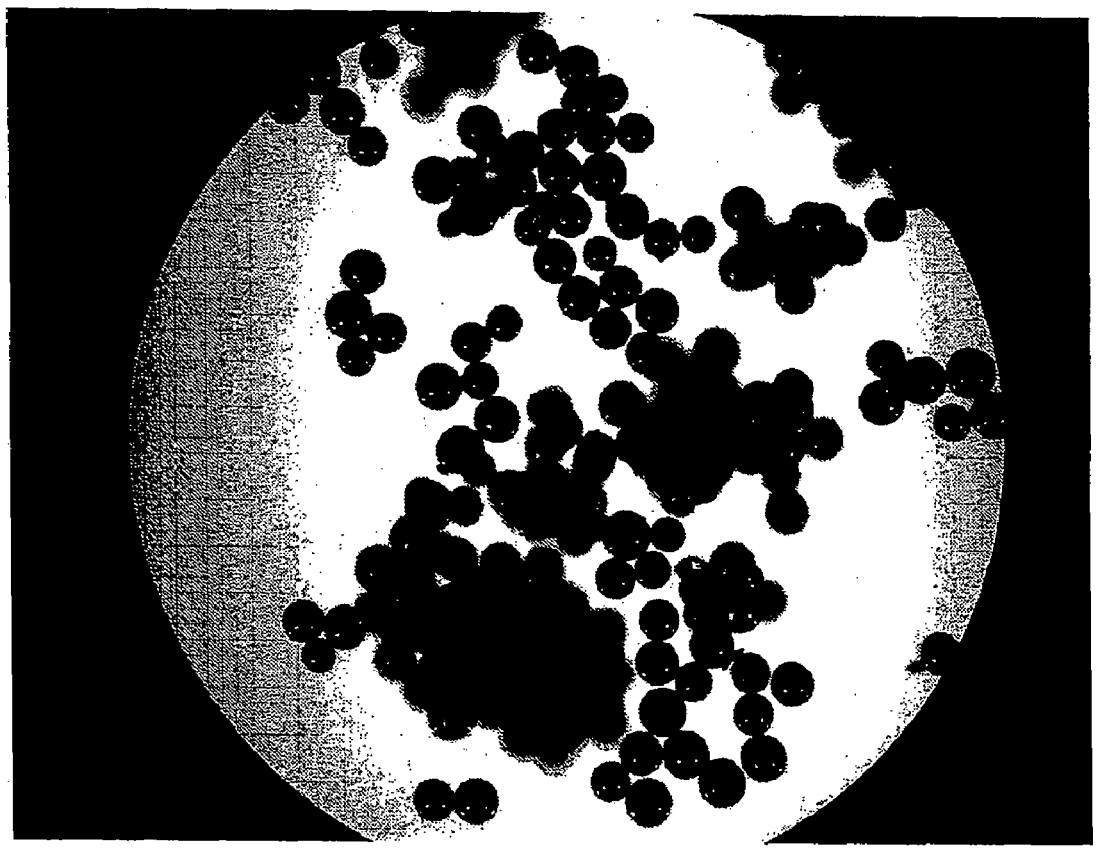
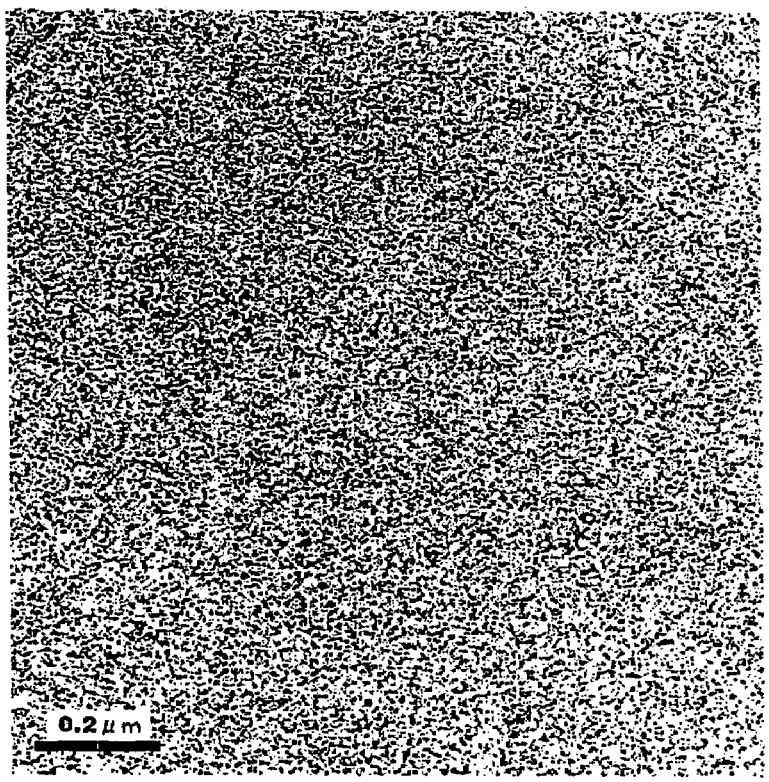
FIGURE 2

RESIN-PLATINUM COMPLEX AND RESIN-SUPPORTED PLATINUM CLUSTER CATALYST

FIELD OF THE INVENTION

The present invention relates to a resin-supported platinum cluster complex in which the platinum clusters are included in a hydrophilic resin and a catalyst thereof. This catalyst provides a green chemistry needed in the area of organic synthesis and other areas.

PRIOR ART

Organic solvents are indispensable in organic synthesis reactions to control the reactions and allow them to proceed efficiently. However, the use of organic solvents has been stringently restricted recently since they are ignitable, toxic to living materials and cause environmental pollution. A means to solve this problem is to develop reactions that proceed in water.

Furthermore, numerous catalytic reactions using homogeneous organometallic reagents were developed for conventional organic synthesis reactions. However, serious problems associated with homogeneous catalysts include difficulties in separating the metal and preventing the metal from remaining in the products. The difficulties meant that metal wastes were formed, and the environmental burden was significant. The current status also means that recovered catalysts are discarded.

Catalysts that solve the problems described above, that is, catalysts that are effective without using an organic solvent from an environmental pollution standpoint and catalysts that can be readily recovered and reused are desired when synthesizing organic compounds.

The inventors have already developed amphoteric resin-supported transition metal catalysts with suitable catalytic actions in water and have previously succeeded in constructing effective organic transformation reactions thereby making possible a reaction that does not use an organic solvent with the recovery-recycling of the catalyst. The inventors, in particular, prepared an amphoteric PS-PEG resin-supported Pd nano particle catalyst that is effective in various organic transformation reactions conducted in water and have already published the findings. (Reference 1) However, this Pd catalyst still has problems. For example, it requires a ligand preparation and the reactions require high temperatures.

Reference 1: Angew. Chem. Int. Ed. 2003, 42, 194.

Problems to be Solved by the Invention

Amphoteric resin-supported transition metal catalysts (Reference 1) are excellent catalysts that are effective in water and can be recovered-reused and can be effectively used in industrial applications, particularly in combinatorial chemical syntheses. However, the focus in the present invention is on the characteristics of the Pt metal, and the objective is to prepare a catalyst with even better activity. Other goals include a simple catalyst preparation that makes ligand preparation unnecessary by directly using a readily available amphoteric resin and the development of a catalyst that effectively functions in water.

In addition, the objective is to establish an entire series of operations including the treatment after the reaction as a reaction system using no organic solvent at all, that is, a completely aqueous reaction-production system by extracting the product incorporated in the amphoteric resin using supercritical carbon dioxide after the reaction.

The objective of the present invention is to provide a resin platinum complex having adequate catalyst activity that is also readily separated from the target material and can be reused.

Means to Solve the Problems

When producing a resin platinum complex using the present invention, a complex of a platinum compound and a hydrophilic resin that contains nitrogen-containing groups such as amino groups and the like is first formed. This complex becomes unstable and is destroyed when the complex is reduced using a reducing agent in an aqueous solvent, and fine platinum particles are enclosed by the hydrophilic resin that is the ligand of the complex. The hydrophilic resin is located on the outside and the platinum is incorporated inside at this point since the solvent is water. That is, finely divided platinum clusters are uniformly dispersed in the hydrophilic resin in the product, and the finely divided platinum clusters are in a state where they are shielded from the solvent (water). The Pt catalyst does not leak out during a reaction when a resin-supported platinum cluster catalyst in such a state is used in water. Therefore, a catalyst comprising a resin platinum complex of the present invention is particularly suited for various reactions when water is the solvent.

That is, the present invention is a method for producing a resin-supported platinum cluster complex comprising the steps of (a) forming a platinum complex represented by the general formula (chemical formula 2)

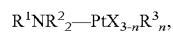

wherein $R^1$ is a carrier containing a hydrophilic polymer chain, $R^2$, may be identical or different, is a hydrogen atom, an alkyl group, an aryl group or —$CONR^4_2$, wherein $R^4$, may be identical or different, is a hydrogen atom, an alkyl group or an aryl group, and, however, $NR^2_2$ may form a pyridine ring, an acridine ring or a quinoline ring, X is a halogen atom, $R^6COO$—, $SO_4$—, CN—, $NO_3$— or SCN—, wherein $R^6$ is an alkyl group or an aryl group, $R^3$ is an unsaturated organic ligand, n is an integer from 0 to 4, from a nitrogen-containing compound represented by the general formula (chemical formula 1)

wherein $R^1$ and $R^2$ are the same as defined above, and a platinum compound represented by the general formula

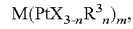

wherein M is an alkali metal, an alkaline earth metal or a quaternary ammonium ion represented by $N+R^5_4$, wherein $R^5$, may be identical or different, is a hydrogen atom, an alkyl group or an aryl group, m is an integer indicating the electrical charge number of M, and X, $R^3$ and n are the same as defined above, and (b) allowing the platinum complex to react with a reducing agent.

In addition, the present invention is a resin-supported platinum cluster complex comprising (a) a platinum particle core having an average diameter of from 1 nm to 10 nm, and (b) a resin layer surrounding the core, comprising a nitrogen-containing compound represented by the general formula $$R^1NR^2_2,$$

wherein $R^1$ and $R^2$ are the same as defined above.

Advantages of the Invention

Organic solvents were traditionally widely used in organic syntheses due to their excellent ability to dissolve, but their use is severely restricted today since they cause environmental pollution and the like.

On the other hand, when a catalyst complex that is only slightly soluble or insoluble in ordinary organic materials is allowed to react in water, two layers separate and the reaction does not proceed well. However, the catalyst of the present invention exhibits effective catalytic action in various reactions that use water as a solvent.

Also, conventional oxidation reactions conducted using chromic acid needed to be anhydrous reactions, but the catalyst of the present invention has the advantage of making such a consideration unnecessary.

Furthermore, the amphoteric resin of the present invention contains hydrophobic and hydrophilic segments and can behave relatively freely in water. In addition, the reaction substrate is present in a concentrated state in the resin due to a hydrophobic interaction. Reactions proceed with good efficiency when a resin plays the role of a type of solvent by supporting a catalyst in the resin.

BRIEF DESCRIPTION OF THE DRAWINGS

FIG. 1 shows a photograph of the particles of the platinum catalyst obtained in Example 1.

FIG. 2 shows a TEM photograph of the catalyst shown in FIG. 1.

DETAILED DESCRIPTION OF THE INVENTION

The resin platinum complex of the present invention is obtained by forming a platinum complex comprising a nitrogen-containing compound and a platinum compound and allowing this platinum complex to react with a reducing agent.

This nitrogen-containing compound is represented by the general formula (Chemical formula 1)

$$R^1NR^2_2$$

$R^1$ represents a carrier containing hydrophilic polymer chains.

As the hydrophilic polymer chains, poly(ethylene glycol) chains, poly(propylene glycol) chains, polyamide chains, polyacrylamide chains, poly(vinyl alcohol) chains, poly(acrylic acid) and the like may be cited. The molecular weight may be from about 1,000 to 100,000, but from about 2,000 to 10,000 is preferred.

As the carrier, hydrophobic carriers such as crosslinked polystyrene, crosslinked polyisobutylene, crosslinked polypropylene, crosslinked polyester, crosslinked polyurethane and the like may be cited. The carriers are ordinarily spherically shaped, and the diameter is from 1 μm to 1 mm but from 50 μm to 500 μm is preferred.

$R^1$ comprises hydrophilic polymer chains and a carrier and may also comprise hydrophilic polymer chains bonded both to a carrier and to $NR^2_2$ groups.

In addition, $R^1$ may be a carrier containing hydrophilic polymer and hydrophobic polymer chains and may also be a carrier in which the hydrophilic polymer chains are connected to $NR^2_2$ with the hydrophobic polymer chains connected to said carrier. The hydrophilic polymer chains and hydrophobic polymer chains may also form a copolymer using block type connections.

As the hydrophobic polymer chains, polymer chains such as styrene, isobutylene, propylene, ester, urethane and the like may be cited. The hydrophilic polymer chains cited above may be used. They may also contain alkyl chains containing one to twenty carbon atoms and aryl groups such as phenyl groups and the like. The molecular weight of the copolymer is from about 1,000 to 100,000, but from about 2,000 to 10,000 is preferred.

The $R^2$'s may be identical or different and $R^2$ represents a hydrogen atom, an alkyl group, an aryl group or —$CONR^4_2$ (in the formula the R4's may be identical or different, and $R^4$ represents a hydrogen atom, an alkyl group or aryl group). At least one of the two $R^2$ groups preferably is a hydrogen atom, and a more preferred situation is for both of them to be hydrogen atoms. However, $NR^2_2$ may also form a pyridine ring, an acridine ring or quinoline ring. It is preferred that the number of carbon atoms in the alkyl group be four or less, and a phenyl group is preferred as the aryl group. The R2's may also contain appropriate substituents.

As a carrier ($R^1$) containing such hydrophilic molecular chains, TentaGel [registered trademark, a polystyrene-poly(ethylene glycol) copolymer resin, amino group concentration 0.31 mmole/g] manufactured by Rapp Polymere GmbH, ArgoGel [registered trademark, a polystyrene-poly(ethylene glycol) copolymer resin, amino group concentration 0.36 mmole/g] manufactured by Argonaut Technologies, Inc., NovaGel [registered trademark, a polystyrene-poly(ethylene glycol) copolymer resin, contains amino groups] manufactured by Novabiochem Corp. and the like, for example, may be cited.

In addition, the platinum compound is represented by the general formula $$M(PtX_{4-n}R^3_n)_m$$

M is an alkali metal, an alkaline earth metal or a quaternary ammonium ion represented by $N+R^5_4$ (in the formula, the $R^5$'s may be identical or different and $R^5$ represents a hydrogen atom, an alkyl group or an aryl group), but an alkali metal is preferred. As the alkali metal, Li, Na, K, Rb and Cs may be cited, and K is preferred. As the alkaline earth metal, Mg, Ca and Ba may be cited.

X represents an anionic ligand such as halogen atom, carboxylic ion, $SO_4$—, CN—, $NO_3$— and SCN—, and halogen atom is preferred. A chlorine atom or a bromine atom is ordinarily used as the halogen atom. As the carboxylic ion, those ordinarily represented by $R^6COO$— (in the formula $R^6$ represents an alkyl group or an aryl group and an alkyl group containing one to twenty carbon atoms, a phenyl group and the like are preferred) may be used.

$R^3$ represents an unsaturated organic ligand, and ethylene, cyclooctene, acetylene and the like, for example, may be cited.

n represents an integer from zero to four and preferably represents zero.

m represents an integer indicating the electrical charge of the metal, M.

The conditions under which the nitrogen-containing compound and the platinum compound are allowed to react are as follows.

The solvent is preferably a highly polar solvent such as, for example, water, DMF, DMSO and methanol, and water is preferred.

The concentrations of the nitrogen-containing compound and the platinum compound are from 0.01 mole/l to 1 mole/l, respectively, but 0.05 mole/l is preferred.

The resin platinum complex can be prepared in air or in an inert gas atmosphere such as nitrogen, argon and the like, but air is preferred.

The preparation temperature for the resin platinum complex is ordinarily from about 0° C. to 100° C., but room temperature is preferred.

The resin platinum complex preparation time is ordinarily from a minute to twenty-four hours, but about an hour is preferred.

The platinum catalysts comprising these nitrogen-containing compounds and platinum compounds are represented by the general formula (Chemical formula 2).

$$E^1NR^2{}_2\text{—}PtX_{3-n}R^3{}_n$$

In the formula, $R^1$-$R^3$, X and n are as defined above.

The platinum complex is allowed to react with a reducing agent.

As the reducing agent, primary alcohols, secondary alcohols and metal hydride compounds such as $NaBH_4$, $NaCNBH_3$, $LiBH_4$, $LiAlH_4$ and the like may be used, and benzyl alcohol is preferred.

As the solvent, polar solvents such as water, THF and $CHCl_3$ may be used, but the reaction is preferably conducted in an aqueous solvent.

The platinum complex concentration is from about 0.01 mole/l to 1 mole/l, but about 0.05 mole/l is preferred.

The atmosphere is air, nitrogen or an inert atmosphere such as argon, but air is preferred. The reaction temperature is ordinarily from 0° C. to 120° C., but about 80° C. is preferred.

The reaction time is ordinarily from an hour to forty-eight hours, but about twelve hours is preferred.

A resin-supported platinum cluster complex comprising a platinum particle core with an average diameter of from 1 nm to 10 nm and a resin layer comprising the aforementioned nitrogen-containing compound (general formula $R^1NR^2{}_2$) surrounding the periphery is obtained as a result of the reaction.

The shape of the catalyst can be easily observed using an ordinary optical microscope. The structure can be confirmed in further detail by using a laser scanning microscope, atomic force microscope or electron microscope.

A catalyst comprising a resin-supported platinum cluster complex obtained in the manner described above displays effective catalytic action in reactions such as oxygen oxidations of alcohols and the like conducted under ambient oxygen pressure, in an air atmosphere or under mild conditions in water.

The following Examples illustrate the present invention, but it is not intended to limit the scope of the invention.

EXAMPLE 1

A platinum complex was obtained by adding 372 mg (1.01 mmoles) of $KPtCl_3(C_2H_4)$ manufactured by Strem Chemicals Inc. to 3.24 g (1.01 mmoles) of TentaGel [registered trademark, a polystyrene-poly(ethylene glycol) copolymer resin, amino group concentration 0.31 mmole/g] manufactured by Rapp Polymere GmbH and shaking the mixture for an hour at room temperature in 20 ml of water.

$^{13}$C-NMR (SR-MAS, $CDCl_3$) δ; 39.9, 44.4, 68.0-73.0, 72.2, 74.0, 104.2, 125.0-130.3, 144.8.

The complex obtained as described above was reduced over twelve hours at 80° C. using an excess of benzyl alcohol, 5 ml, and 24 ml of water. The reaction equation and the analytical results of the product are shown below.

[Chemical Equation 1]

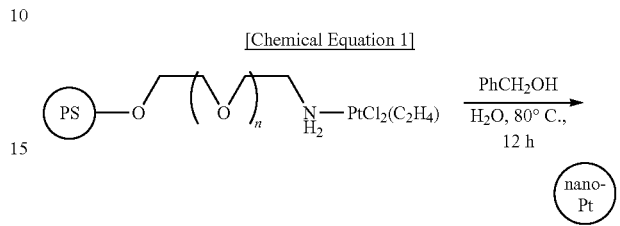

$^{13}$C-NMR (SR-MAS, $CDCl_3$) δ; 39.0-42.0, 44.4 (—O$CH_2\underline{C}H_2NH_2$), 68.0-72.0 (PEG), 72.2 (—O$\underline{C}H_2CH_2NH_2$), 74.0 ($H_2C=CH_2$), 103-105, 125.0-133.3, 143.0-148.0.

The catalyst obtained was in the form of platinum supported on a polymer, and it is depicted in FIGS. 1 and 2.

FIG. 1 is a photograph taken at ×160 magnification using an optical microscope (manufactured by Nikon, SMZ1500). The catalyst produced is in the form of a dispersion of platinum clusters in PS-PEG resin beads with a diameter of 90 μm. FIG. 2 shows the results observed when a field emission transmittance type electron microscope (manufactured by JEOL, JEM-2100F) was used at ×15,000 magnification. The examination using the transmission type electron microscope indicated that fine Pt cluster particles with an average particle size of 4.5 nm were uniformly dispersed in the resin. That is, the platinum clusters were covered with the PS-PEG resin and were considered uniformly dispersed over the entire PS-PEG resin beads.

EXAMPLE 2

In an ambient pressure oxygen atmosphere, 121 μl of 1-phenyl ethanol and 173.7 mg of the platinum catalyst obtained in Example 1 were agitated for twenty-four hours at 60° C. in 10 ml of water. The reaction mixture was subsequently extracted using ethyl acetate, and the organic layer was dried using magnesium sulfate and filtered to obtain 98.9 mg (82% yield) of acetophenone. The reaction equation and the analytical results of the product are shown below.

[Chemical Equation 2]

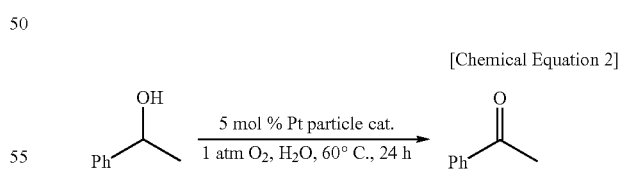

$^1$H-NMR (400 MHz, solvent:$CDCl_3$) δ: 2.61 (s, 3H), 7.47 (t, 2H, J=7.56 Hz), 7.57 (t, 1H, J=7.07, 7.56 Hz), 7.96 (d, 2H, J=8.29 Hz); MS (m/z) 43, 51, 63, 77, 91, 105 (ArCO+), 120 (M+)

EXAMPLE 3

The catalyst was recovered upon filtering the reaction product described in Example 2. After drying the catalyst under reduced pressure, the catalyst was again agitated for twenty-four hours at 60° C. in 10 ml of water with 121 μl of 1-phenyl ethanol. Using the same operations subsequently, an ethyl acetate solution containing 97.1 mg (81% yield) of acetophenone was obtained. This catalyst recycling experiment was repeated five times, and the yields were 82%, 81%, 84%, 92% and 90%.

EXAMPLE 4

In an ambient pressure oxygen atmosphere, 26.4 mg of cyclooctanol and 34.1 mg of the platinum catalyst obtained in Example 1 were agitated for twelve hours at 60° C. in 2 ml of water. The reaction mixture was subsequently extracted using ethyl acetate, and the organic layer was dried using magnesium sulfate, filtered and concentrated to obtain 22.6 mg (87% yield) of cyclooctanone. The reaction equation and the analytical results of the product are shown below.

[Chemical Equation 3]

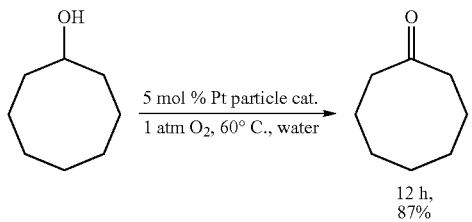

12 h, 87%

$^1$H-NMR (400 MHz, solvent:CDCl$_3$) δ: 1.25 (t, 2H, J=11.8 Hz), 1.33-1.40 (m, 4H), 1.50-1.57 (m, 4H), 1.84-1.90 (m, 4H), 2.40 (t, 4H, J=6.2 Hz); MS (m/z) 42, 55, 69, 83, 98, 111, 126 (M+)

EXAMPLE 5

In an ambient pressure oxygen atmosphere, 25 mg of cyclooctanol and 137 mg of the platinum catalyst obtained in Example 1 were agitated for sixty hours at 60° C. in 2 ml of water. The reaction mixture was subsequently extracted using ethyl acetate, and the organic layer was dried using magnesium sulfate, filtered and concentrated to obtain 22.8 mg (93% yield) of cyclooctanone.

EXAMPLE 6

In an ambient pressure oxygen atmosphere, 40.3 mg of cinnamyl alcohol, 105.3 mg of the platinum catalyst obtained in Example 1 and 40.2 mg of potassium carbonate were agitated for eighteen hours at 60° C. in 3 ml of water. The aqueous layer was subsequently washed using tert-butyl methyl ether and was extracted using ethyl acetate after neutralizing the layer with a HCl solution. The ethyl acetate solution was dried using magnesium sulfate, filtered and concentrated to obtain 41.5 mg (93% yield) of cinnamic acid. The reaction equation and the analytical results of the product are shown below.

[Chemical Equation 4]

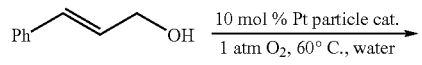

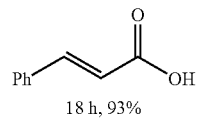

18 h, 93%

$^1$H-NMR (500 MHz, solvent:CDCl$_3$) δ: 6.46 (d, 1H, J=15.9 Hz), 7.40-7.45 (m, 3H), 7.55-7.57 (m, 2H), 7.79 (d, 1H, J=15.9 Hz)

EXAMPLE 7

In an ambient pressure oxygen atmosphere, 29.2 mg of 4-phenyl-but-3-ene-2-ol and 33.9 mg of the platinum catalyst obtained in Example 1 were agitated for fifteen hours at 60° C. in 2 ml of water. The reaction mixture was subsequently extracted using ethyl acetate, and the organic layer was dried using magnesium sulfate, filtered and concentrated to obtain 25.2 mg (87% yield) of benzalacetone. The reaction equation and the analytical results of the product are shown below.

[Chemical Equation 5]

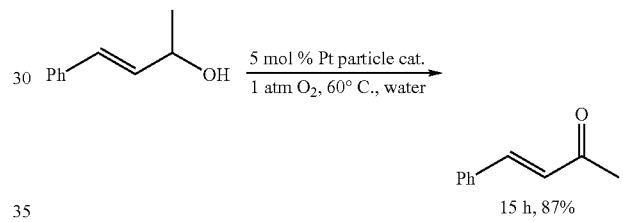

15 h, 87%

$^1$H-NMR (500 MHz, solvent:CDCl$_3$) δ: 2.39 (s, 3H), 6.73 (d, 1H, J=16.5 Hz), 7.38 (m, 3H), 7.47-7.58 (m, 3H); MS (m/z) 39, 51, 63, 77, 91, 103, 115, 131, 145 (M+)

EXAMPLE 8

In an ambient pressure oxygen atmosphere, 26.9 mg of 2-octanol and 35.3 mg of the platinum catalyst obtained in Example 1 were agitated for fifteen hours at 60° C. in 2 ml of water. The reaction mixture was subsequently extracted using ethyl acetate, and the organic layer was dried using magnesium sulfate, filtered and concentrated to obtain 22.6 mg (85% yield) of 2-octanone. The reaction equation and the analytical results of the product are shown below.

[Chemical Equation 6]

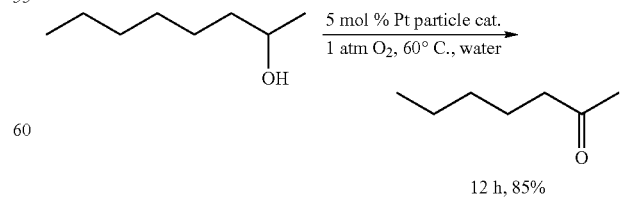

12 h, 85%

$^1$H-NMR (500 MHz, solvent:CDCl$_3$) δ: 0.88 (t, 3H, J=6.7 Hz), 1.23-1.38 (m, 6H), 1.54-1.60 (m, 2H), 2.14 (s, 3H), 2.42 (t, 2H, J=7.4 Hz); MS (m/z) 43, 58, 71, 85, 99, 113, 128 (M+)

EXAMPLE 9

In an ambient pressure oxygen atmosphere, 46.5 mg of 1-phenyl octanol and 156.4 mg of the platinum catalyst obtained in Example 1 were agitated for thirty-six hours at 60° C. in 2.3 ml of water. The reaction mixture was subsequently filtered to separate the catalyst and the water. The aqueous layer was concentrated under reduced pressure, and the product retaining the catalyst was extracted using super critical carbon dioxide to obtain 41.9 mg (91% yield) of 1-octaphenone. The reaction equation and the analytical results of the product are shown below.

[Chemical Equation 7]

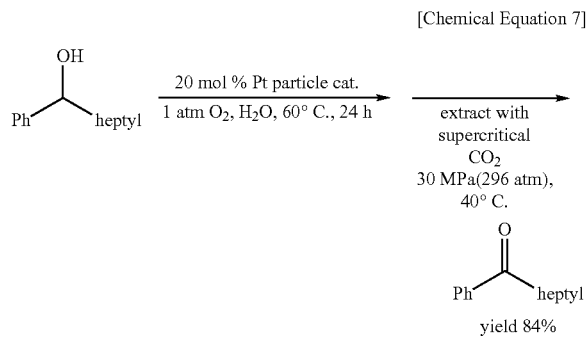

$^1$H-NMR (500 MHz, solvent:CDCl$_3$) δ: 0.89 (t, 3H, J=6.7 Hz), 1.25-1.41 (m, 8H), 1.74 (quintet, 2H, J=), 2.96 (t, 2H, J=7.3 Hz), 7.46 (t, 2H, J=7.9 Hz), 7.55 (t, 1H, J=7.3, 7.9 Hz), 7.96 (d, 2H, J=7.3 Hz); $^{13}$C-NMR (126 MHz; solvent: CDCl$_3$) δ: 14.1, 22.6 24.4, 29.1, 29.3, 31.7, 38.6, 128.0, 128.5, 132.8, 137.1, 200.6; MS (m/z) 41, 51, 65, 77, 91, 105 (ArCO+), 120, 133, 204 (M+)

As indicated above, oxidation reactions proceed by simply agitating the catalyst of the present invention along with a substrate in an oxygen atmosphere in water. Upon completion of the reaction the reaction product is concentrated in the resin and can be separated from water by simply filtering. By subsequently extracting the reaction product from the resin using, for example, super critical carbon dioxide the reaction product and the catalyst can be easily separated. The recovered catalyst can be reused.

What is claimed is:

1. A method for producing a resin-supported platinum cluster complex comprising the steps of:
   (a) forming a platinum complex represented by the general formula (chemical formula 2)

$R^1NR^2{}_2$—$PtX_{3-n}R^3{}_n$, wherein $R^1$ comprises a carrier and a hydrophilic polymer chain, wherein the carrier is hydrophobic and the hydrophilic polymer chain is connected both to the carrier and to the $NR^2{}_2$ group and the molecular weight of $R^1$ is about 1,000 to 100,000, $R^2$, may be identical or different, is a hydrogen atom, an alkyl group, an aryl group, and, however, $NR^2{}_2$ may form a pyridine ring, an acridine ring or a quinoline ring, X is a halogen atom, $R^6COO^-$, $SO_4{}^-$, $CN^-$, $NO_3{}^-$ or $SCN^-$, wherein $R^6$ is an alkyl group or an aryl group, $R^3$ is an unsaturated hydrocarbon ligand, n is an integer from 0 to 3,
   from a nitrogen-containing compound represented by the general formula (chemical formula 1)

$R^1NR^2{}_2$, wherein $R^1$ and $R^2$ are the same as defined above, and
   a platinum compound represented by the general formula $M(PtX_{3-n}R^3{}_n)_m$, wherein M is an alkali metal, an alkaline earth metal or a quaternary ammonium ion represented by $N^+R^5{}_4$, wherein $R^5$, may be identical or different, is a hydrogen atom, an alkyl group or an aryl group, m is an integer indicating the electrical charge number of M, and X, $R^3$ and n are the same as defined above, and
   (b) allowing the platinum complex to react with a reducing agent to produce the resin-supported platinum cluster complex containing a platinum particle core with an average diameter of from 1 nm to 10 nm.

2. The method of claim 1 wherein the reaction of the platinum complex and the reducing agent is conducted in an aqueous solvent.

3. The method of claim 1 wherein $R^1$ is a carrier containing a hydrophilic polymer chain and a hydrophobic polymer chain, wherein the carrier is hydrophobic, the hydrophilic polymer chain and the hydrophobic polymer chain are connected in blocks to form a copolymer, the hydrophilic polymer chain is connected to the $NR^2{}_2$ group and the hydrophobic polymer chain is connected to the carrier.

4. The method of claim 1 wherein the hydrophilic polymer chain is poly(ethylene glycol) chain.

5. A resin-supported platinum cluster complex catalyst comprising a complex comprising
   (a) a platinum particle core having an average diameter of from 1 nm to 10 nm, and
   (b) a resin layer surrounding the core, comprising a nitrogen-containing compound represented by the general formula $R^1NR^2{}_2$, wherein $R^1$ comprises a carrier and a hydrophilic polymer chain, wherein the carrier is hydrophobic and the hydrophilic polymer chain is connected both to the carrier and to the $NR^2{}_2$ group and the molecular weight of $R^1$ is about 1,000 to 100,000, and the $R^2$, may be identical or different, is a hydrogen atom, an alkyl group, an aryl group, and, however, $NR^2{}_2$ may form a pyridine ring, an acridine ring or a quinoline ring that may contain substituents.

6. The resin-supported platinum cluster catalyst of claim 5 wherein $R^1$ is a carrier containing a hydrophilic polymer chain and a hydrophobic polymer chain, wherein the carrier is hydrophobic, the hydrophilic polymer chain and the hydrophobic polymer chain are connected in blocks to form a copolymer, the hydrophilic polymer chain is connected to the $NR^2{}_2$ group and the hydrophobic polymer chain is connected to the carrier.

7. The resin-supported platinum cluster catalyst of claim 5 wherein the hydrophilic polymer chain is poly(ethylene glycol) chain.

8. A resin-supported platinum cluster catalyst comprising the resin-supported platinum cluster complex produced by the method of claim 1.

9. The resin-supported platinum cluster complex catalyst of claim 6, wherein the hydrophilic polymer chain is poly (ethylene glycol) chain.

10. The resin-supported platinum cluster catalyst comprising the resin-supported platinum cluster complex produced by the method of claim 3.

11. The resin-supported platinum cluster catalyst comprising the resin-supported platinum cluster complex produced by the method of claim 4.

12. A process comprising reacting an alcohol with oxygen in the presence of the catalyst of claim 8.

13. A process comprising reacting an alcohol with oxygen in the presence of the catalyst of claim 5.

* * * * *